(12) United States Patent
Lee et al.

(10) Patent No.: US 11,692,171 B2
(45) Date of Patent: Jul. 4, 2023

(54) PREPARATION METHOD OF HUMAN-DERIVED CARDIAC STEM CELL SPHEROID AND USE THEREOF

(71) Applicants: INJE UNIVERSITY INDUSTRY-ACADEMIC COOPERATION FOUNDATION, Gimhae-si (KR); HIERABIO INC., Seoul (KR)

(72) Inventors: Seung Jin Lee, Seoul (KR); Young-il Yang, Busan (KR)

(73) Assignees: INJE UNIVERSITY INDUSTRY-ACADEMIC COOPERATION FOUNDATION, Gimhae-si (KR); HIERABIO INC., Seoul (KR)

( * ) Notice: Subject to any disclaimer, the term of this patent is extended or adjusted under 35 U.S.C. 154(b) by 467 days.

(21) Appl. No.: 16/627,258

(22) PCT Filed: Jun. 29, 2018

(86) PCT No.: PCT/KR2018/007433
§ 371 (c)(1),
(2) Date: Dec. 27, 2019

(87) PCT Pub. No.: WO2019/004792
PCT Pub. Date: Jan. 3, 2019

(65) Prior Publication Data
US 2020/0131479 A1 Apr. 30, 2020

(30) Foreign Application Priority Data
Jun. 30, 2017 (KR) .................. 10-2017-0083057

(51) Int. Cl.
*C12N 5/0775* (2010.01)
*C12N 5/077* (2010.01)
*A61K 35/34* (2015.01)

(52) U.S. Cl.
CPC ............ *C12N 5/0662* (2013.01); *A61K 35/34* (2013.01); *C12N 5/0657* (2013.01); *C12N 2513/00* (2013.01)

(58) Field of Classification Search
CPC . C12N 5/0662; C12N 5/0657; C12N 2513/00
See application file for complete search history.

(56) References Cited

U.S. PATENT DOCUMENTS

2008/0267921 A1  10/2008  Marban et al.
2016/0244723 A1  8/2016  Giacomello et al.

FOREIGN PATENT DOCUMENTS

| CN | 104922155 A | 9/2015 |
| JP | 2012-523238 A | 10/2012 |
| KR | 10-2013-0124075 A | 11/2013 |
| WO | 2014-141220 A1 | 9/2014 |

OTHER PUBLICATIONS

Oltolina et al., (2015) Human cardiac progenitor spheroids exhibit enhanced engraftment potential. PLoS One, 10(10) e0141632. (Year: 2015).*
Chimenti et al., (2014) Serum and supplement optimization for EU GMP-compliance in cardiospheres cell culture. Journal of Cellular and Molecular Medicine, 18(4) pp. 624-634. (Year: 2014).*

* cited by examiner

*Primary Examiner* — Kara D Johnson
(74) *Attorney, Agent, or Firm* — Seed IP Law Group LLP (57) ABSTRACT

The present invention relates to a preparation method of a spheroid using human-derived cardiac stem cells and a therapeutic use for ischemic heart disease using the myocardial regeneration effect thereof. The spheroid using the cardiac stem cells provided in the present invention has excellent myocardial differentiation ability and regenerative therapeutic ability as compared to existing cardiac stem cells, and thus may be used for the treatment of ischemic heart disease such as myocardial infarction.

9 Claims, 10 Drawing Sheets

PREPARATION METHOD OF HUMAN-DERIVED CARDIAC STEM CELL SPHEROID AND USE THEREOF

TECHNICAL FIELD

The present invention relates to a preparation method of a spheroid using human-derived cardiac stem cells and a therapeutic use for ischemic heart disease using the myocardial regeneration effect thereof.

BACKGROUND ART

Ischemic heart disease is a disease that occurs because blood supply to part of the heart muscle is insufficient due to the narrowing of blood vessels (coronary arteries) that supply blood to the heart. It is characterized by abnormalities in the heart due to the insufficiency of blood supply such that oxygen and nutrients necessary for the heart are not provided properly, and types of ischemic heart disease include stable angina, unstable angina, variant angina, acute myocardial infarction, etc.

There are two main causes of the narrowing of coronary arteries: organic stenosis and functional spasm, and organic stenosis is the narrowing of the lumen because something accumulates in the blood vessel, and functional spasm is the narrowing of the lumen due to constriction of coronary arteries.

For treatment methods of ischemic heart disease, there is a method of using drugs that reduce myocardial oxygen consumption to prevent the disease caused by organic stenosis, or a method of using drugs that inhibit spasms to reduce the disease. However, drugs are not effective for tissues that have already necrosed due to the insufficiency of blood supply, and thus there is a need for new treatment methods of ischemic heart disease.

With regard to recent stem cell therapies, it is possible to recover the function of cells and tissues in cases where the recovery and regeneration of lost cells are essential such as neurological disease, heart disease, lung disease, liver disease, and cancer, and also the recovery does not progress naturally, and additional studies related thereto are actively in progress (Segers, Vincent F M and Richard T Lee, Nature 451.7181 (2008): 937-942.). It has been found that for ischemic diseases, adipose, bone marrow, or umbilical cord blood-derived stem cell therapeutic agents can be used, and blood vessels can be regenerated. However, in the case of general monolayer culture, most of stem cells transplanted to the ischemic site are killed, and thus, it has a problem where the therapeutic effect as a cell therapeutic agent is not great. As monolayer culture is difficult for mass culture, it is not suitable for clinical treatment, and thus its clinical application has been difficult.

DISCLOSURE

Technical Problem

The present inventors have made diligent efforts to develop a composition capable of preventing or treating ischemic heart disease. As a result, the present inventors found a method of efficiently producing cardiac stem cell spheroids and completed the present invention by confirming that the corresponding spheroids have an excellent effect of treating ischemic heart disease.

Technical Solution

An object of the present invention is to provide a pharmaceutical composition for preventing or treating ischemic heart disease, comprising a cardiac stem cell spheroid as an effective component, wherein the cardiac stem cell spheroid is prepared by a preparation method comprising 1) seeding cardiac stem cells (CSC) in a culture vessel comprising a medium and inhibiting cell adhesion at a seeding density of $1 \times 10^2$ cells/cm$^2$ to $2 \times 10^5$ cells/cm$^2$; and 2) obtaining a spheroid by culturing the culture vessel in which the cardiac stem cells are seeded within 3 days.

Another object of the present invention is to provide a method for preparing a cardiac stem cell spheroid, comprising 1) seeding cardiac stem cells (CSC) in a culture vessel comprising a medium and inhibiting cell adhesion at a seeding density of $1 \times 10^2$ cells/cm$^2$ to $2 \times 10^5$ cells/cm$^2$; and 2) obtaining a spheroid by culturing the culture vessel in which the cardiac stem cells are seeded within 3 days.

Still another object of the present invention is to provide a cardiac stem cell spheroid, prepared by the above preparation method.

Advantageous Effect

The spheroid using cardiac stem cells provided in the present invention have superior myocardial differentiation ability and regenerative therapeutic ability as compared to existing cardiac stem cells, and thus, it may be used for the treatment of ischemic heart diseases such as myocardial infarction.

BEST MODE

In one aspect of achieving the above objects, the present invention provides a method for preparing a cardiac stem cell spheroid, comprising 1) seeding cardiac stem cells (CSC) in a culture vessel comprising a medium and inhibiting cell adhesion at a seeding density of $1 \times 10^2$ cells/cm$^2$ to $2 \times 10^5$ cells/cm$^2$; and 2) obtaining a spheroid by culturing the culture vessel in which the cardiac stem cells are seeded within 3 days.

Hereinafter, the preparation method of cardiac stem cell spheroids in the present invention will be described in detail.

As used herein, the term "cardiac stem cell" refers to a stem cell isolated from a cardiac tissue and can be effectively used for regenerative treatment of a damaged heart due to its superior myocardial differentiation ability as compared to other stem cells.

For the cardiac stem cells of the present invention, human-derived cardiac stem cells that were obtained through human heart tissue and grown through culture were used.

As used herein, the term "medium" refers to a liquid or solid material in which nutrients, osmotic pressure, pH, etc. are adjusted at levels necessary for culture according to the purpose of proliferation, preservation, transplantation, etc. of cells, tissues, or bacteria.

The medium of the present invention includes Dulbecco's modified Eagle's medium (DMEM), calf serum, DMSO, and L-ascorbic acid.

In the present invention, it may be preferable that the medium for culturing cardiac stem cells contains a relatively low concentration of serum. Specifically, the medium of the present invention may include serum at a concentration of 0.1% to 5%, more specifically, may include serum at a concentration of 0.1% to 1%, and even more specifically, may include serum at a concentration of 1%.

Figure 2:
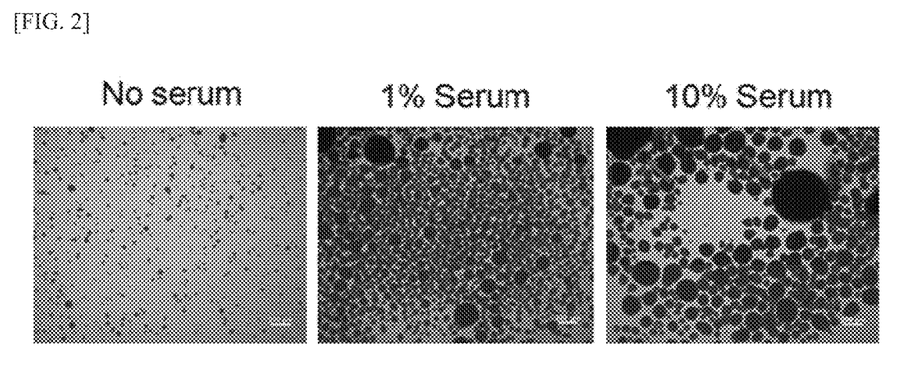
FIG. 2 is a graph showing the formation ability of cardiac stem cell spheroids according to serum concentration: No serum: no serum is added, 1% serum: 1% serum is added, 10% serum: 10% serum is added.

In one embodiment of the present invention, as a result of confirming the effect of serum concentration on the formation of cardiac stem cell spheroids by varying the concentration of serum, spheroids were not formed in the medium without serum, and it was confirmed that spheroids were not uniformly formed at a serum concentration of 10% that is generally used in conventional cell culture. On the other hand, by confirming that uniform cardiac stem cell spheroids were formed at a serum concentration of 1% corresponding to a low concentration, it was confirmed that low concentrations of serum conditions are preferred (FIG. 2).

As used herein, the term "inhibition of cell adhesion" means that the absorption of substances involved in cell adhesion is suppressed due to very high hydrophilicity or hydrophobicity, thereby inhibiting the adhesion of cells to the culture vessel during cell culture, which induces cells to be cultured dimensionally in the medium.

The cell adhesion-inhibition container of the present invention may be HEMA polymer, 2-Methacryloyloxyethyl phosphorylcholine polymer, lipidure coat(amsbio), Nunc HydroCell Surface, Corning, Ultra-Low Attachment Surface, etc., but is not limited thereto.

In one embodiment of the present invention, the cardiac stem cell spheroids were prepared by dimensionally culturing cardiac stem cells through a cell adhesion-inhibition container.

The spheroids prepared by the above preparation method may have a size 200 μm or less, specifically, a size of 50 μm to 200 μm, more specifically, 100 μm to 200 μm, and even more specifically, 150 μm to 200 μm. In addition, the spheroid may have a cell number of 2,000 or less, specifically, a cell number of 100 to 2,000, and more specifically, a cell number of 500 to 2,000, but is not limited thereto.

Figure 4:
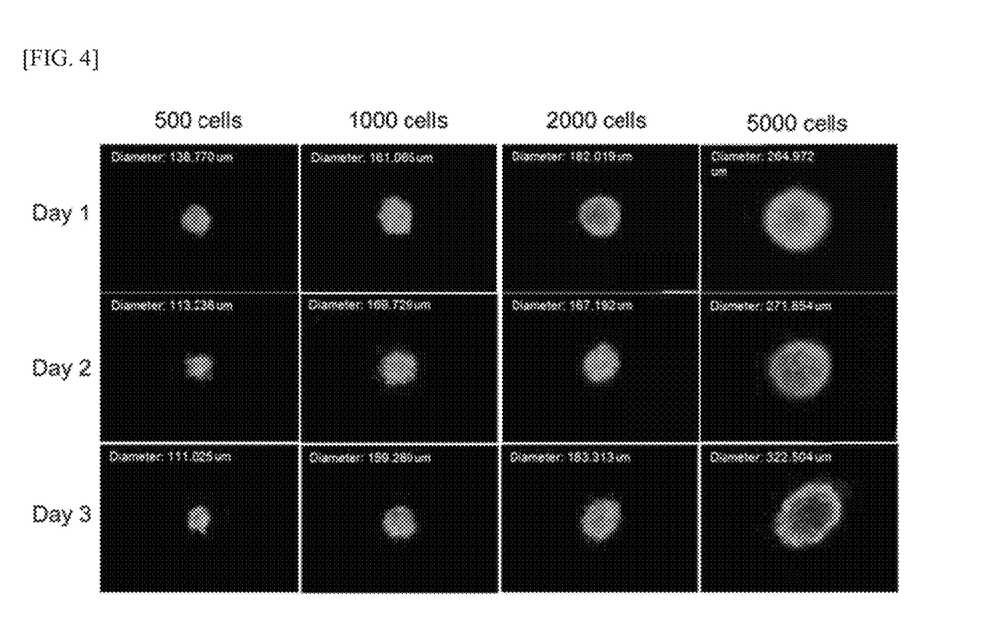
FIG. 4 is a graph showing cell damage of cardiac stem cell spheroids according to the spheroid size.

In one embodiment of the present invention, as a result of confirming the cardiac stem cell damage according to the size of spheroids, for the spheroid of a size of 200 μm or a cell number of 2,000 or more, the necrosis of cells was confirmed in the center, and it was confirmed that the efficient size of spheroids is 200 μm or less or a cell number of 2,000 or less (FIG. 4).

As used herein, the term "seed" refers to the addition of desired cells to a medium prepared for the culturing of cells.

For preparing spheroids at efficient sizes, the seeding density of the present invention may be $1 \times 10^2$ cells/cm$^2$ to $2 \times 10^5$ cells/cm$^2$, specifically, $1 \times 10^3$ cells/cm$^2$ to $2 \times 10^5$ cells/cm$^2$, more specifically, $1 \times 10^4$ cells/cm$^2$ to $2 \times 10^4$ cells/cm$^2$, even more specifically, $0.5 \times 10^5$ cells/cm$^2$ to $2 \times 10^5$ cells/cm$^2$, and even more specifically $1 \times 10^5$ cells/cm$^2$ to $2 \times 10^5$ cells/cm$^2$, but is not limited thereto.

Specifically, for the seeding density to achieve the objects of the present invention, the seeding density which is the upper limit is preferably $2.5 \times 10^5$ cells/cm$^2$, and the necrosis of cells in the center of spheroids may occur at a seeding density of $2.5 \times 10^5$ cells/cm$^2$ or more.

Figure 5:
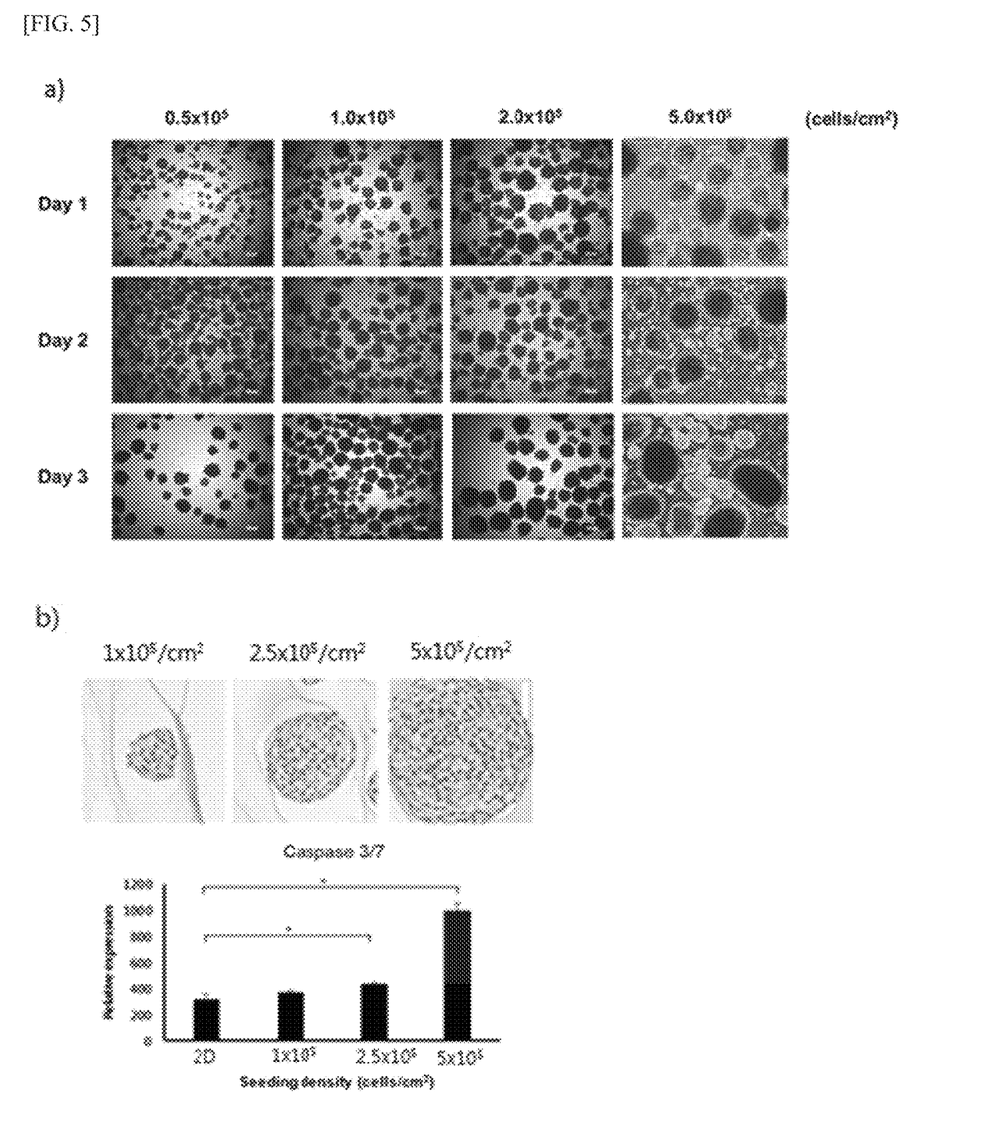
FIG. 5 is a graph showing cell damage of spheroids according to the seeding density of cardiac stem cells; a) the size of cardiac stem cell spheroids according to the seeding density and the culture period, b) caspase 3/7 activity according to the seeding density.

In one embodiment of the present invention, as a result of preparing spheroids by culturing cardiac stem cells at various seeding densities to confirm cell damage according to seeding densities, when the seeding density exceeds $2.5 \times 10^5$ cells/cm$^2$, it was confirmed that the activity of caspase 3/7 for quantifying apoptosis change was increased, and it was confirmed that it is preferable to use a seeding density of $2.5 \times 10^5$ cells/cm$^2$ or less for the efficient preparation of spheroids (FIG. 5).

Figure 6:
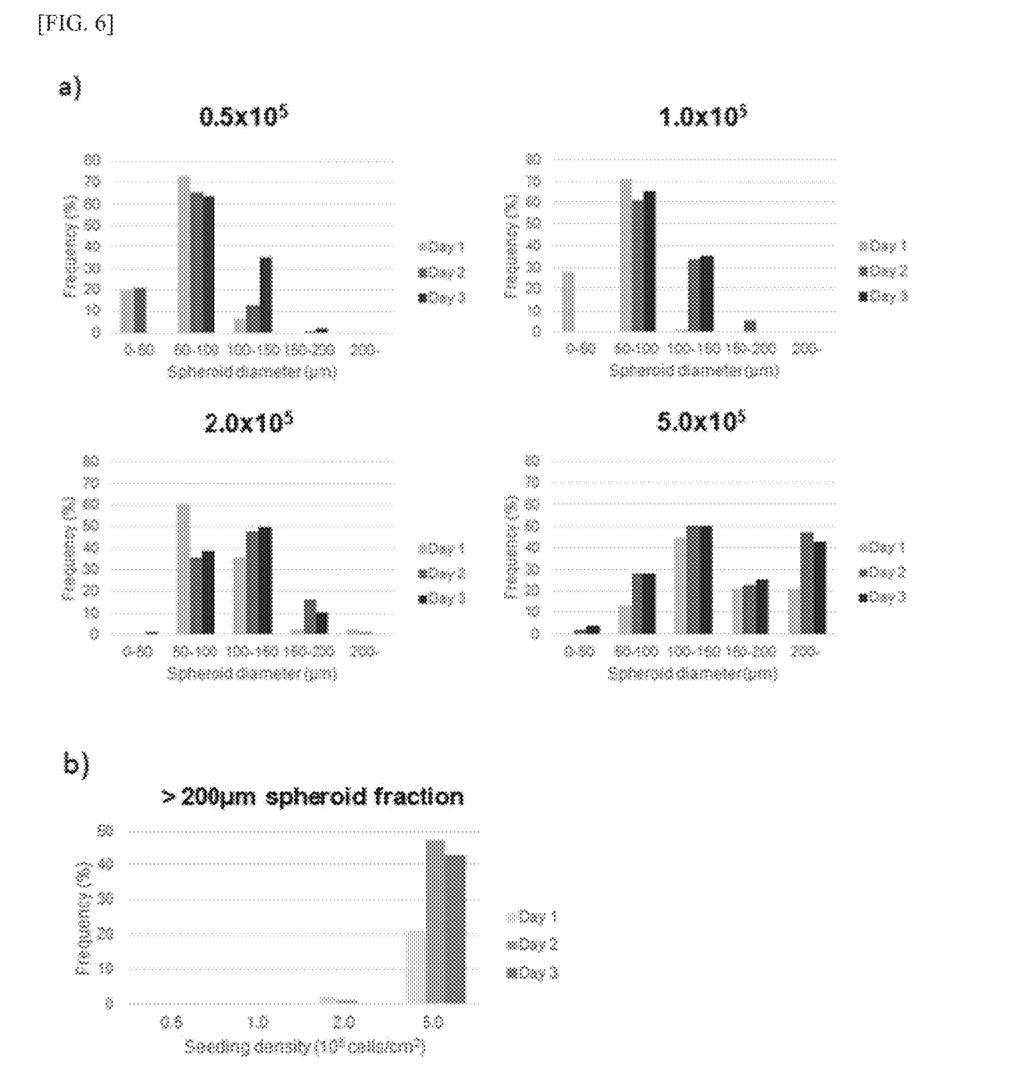
FIG. 6 is a graph showing the distribution of spheroid size by the seeding density and the size change of spheroids by culture period; a) distribution of spheroid size according to seeding density and culture period, b) formation frequency of spheroids having a size of 200 μm or more according to seeding density and culture period.

In one embodiment of the present invention, as a result of confirming the size of spheroids everyday for 3 days by culturing cardiac stem cells at various seeding densities to confirm the size distribution of spheroids according to seeding densities and culture period, it was confirmed that whereas spheroids of 200 μm or more are rarely formed in which cell necrosis occurs at a seeding density of $2.5 \times 10^5$ cells/cm$^2$ or less, remarkably high spheroid fractions of 200 μm were confirmed at a seeding density of $5 \times 10^5$ cells/cm$^2$ or more (FIG. 6).

Meanwhile, unlike the upper limit of the seeding density, the seeding density which is the lower limit is not limited and may vary depending on various conditions. Specifically, while it is preferable to be $0.5 \times 10^5$ cells/cm$^2$, the object of the present invention can be achieved even when seeding at a much lower seeding density depending on the conditions of the culture vessel, for example, the curved surface and height of the culture vessel.

Unlike conventional culture periods for normal cells of 3 to 7 days, the culture period of the present invention may be within 3 days, specifically 1 to 3 days, but is not limited thereto.

Figure 3:
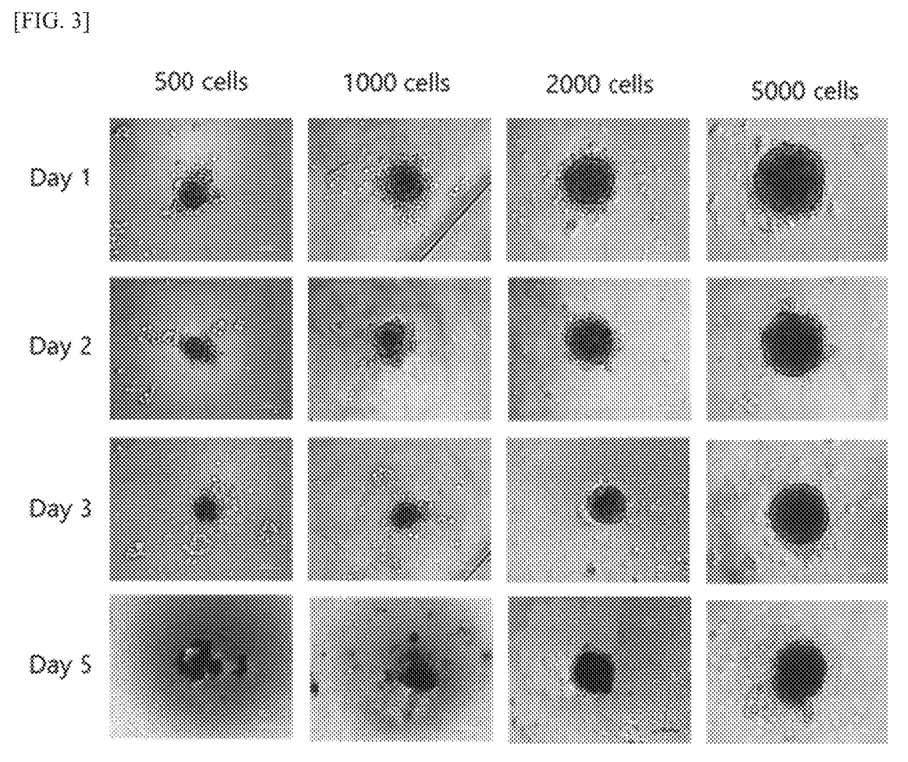
FIG. 3 is a graph showing cell damage of cardiac stem cell spheroids according to the culture period; 500, 1,000, 2,000, 5,000: number of cells constituting spheroids.

In one embodiment of the present invention, as a result of confirming the change of spheroids according to the culture period, it showed a trend where the size of spheroids increased as the culture period became longer, and by confirming that cell necrosis occurred for spheroids of a certain size or more, it was confirmed that it was effective to set the culture period of spheroids to within 3 days (FIG. 3).

In another aspect, the present invention provides a cardiac stem cell spheroid prepared according to the preparation method.

As used herein, the term "cardiac stem cell spheroid" refers to a cell mass of a spherical form prepared by dimensionally culturing cardiac stem cells.

The cardiac stem cell spheroid of the present invention has a high engraftment rate and excellent myocardial regeneration ability compared to the existing cardiac stem cells, and thus can be used for myocardial-related diseases.

In another aspect, the present invention provides a pharmaceutical composition for preventing or treating ischemic heart disease comprising the cardiac stem cell spheroid.

The terms used in the present invention "cardiac stem cell", "medium", "cell adhesion inhibition", "seeding", and "cardiac stem cell spheroid" are as described above.

As used herein, the term "ischemic heart disease" is a disease that occurs because blood supply to part of the heart muscle is insufficient due to the narrowing of blood vessels (coronary arteries) that supply blood to the heart. It is characterized by abnormalities in the heart due to the insufficiency of blood supply such that oxygen and nutrients necessary for the heart are not provided properly, and types of ischemic heart disease include stable angina, unstable angina, variant angina, acute myocardial infarction, etc.

The cardiac stem cell spheroid included in the composition of the present invention may have improved cardiac engraftment ability and myocardial regeneration ability compared to cardiac stem cells that were cultured by monolayer culture.

Figure 8:
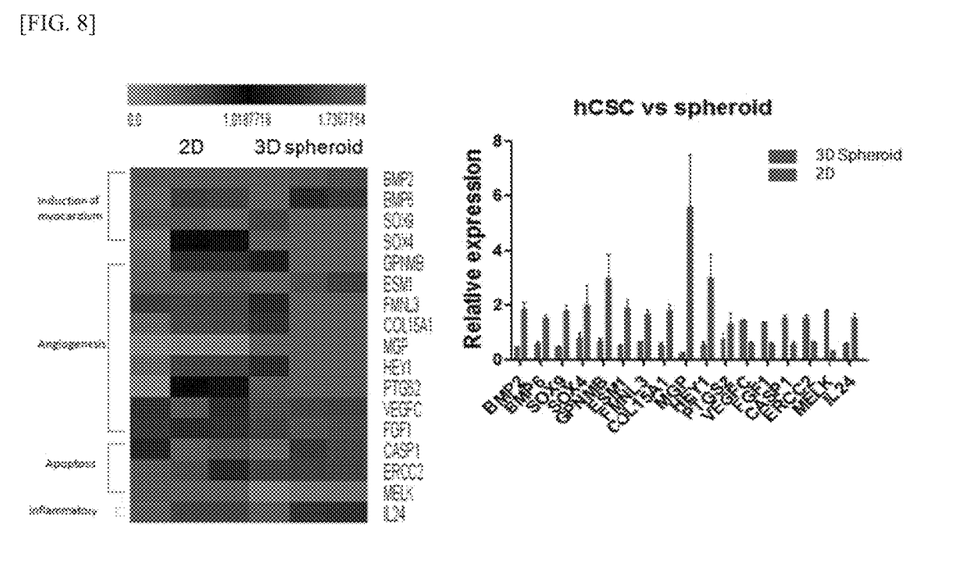
FIG. 8 is a graph comparing the expression levels of pharmacological activation factors of cardiac stem cell spheroids and monolayer culture: 2D: cardiac stem cell monolayer culture, 3D spheroid: cardiac stem cell spheroid.

In one embodiment of the present invention, as a result of comparing the pharmacological activity of cardiac stem cell spheroids with cardiac stem cells that were monolayer-cultured, the expression of myocardial differentiation factor and angiogenesis factors increased, and the expression of apoptosis-related factors decreased. As the expression of anti-inflammatory and immunosuppressive cytokines was increased, it was confirmed that the cell characteristics were changed in the direction of increasing myocardial differentiation ability and regenerative treatment ability for the treatment of ischemic heart disease (FIG. 8).

As used herein, the term "prevention" may mean any action of injecting the composition of the present invention into a subject to inhibit or delay the onset of ischemic heart disease.

As used herein, the term "treatment" may refer to any action of administering the composition of the present invention to an individual suspected of developing ischemic heart disease to improve or ameliorate the symptoms of ischemic heart disease.

The pharmaceutical composition of the present invention may also be used as a single agent, and may be prepared and used in a combination formulation, further including a drug known to have an official ischemic heart disease treatment effect, and may be prepared in unit dose form or in a multi-dose container by being formulated using pharmaceutically acceptable carriers or excipients.

As used herein, the term "pharmaceutically acceptable carrier" may refer to a carrier or a diluent that does not interfere with the biological activity and properties of a compound to be injected without stimulating organisms. The type of carrier that can be used in the present invention is not particularly limited, and any carrier can be used as long as it is a conventionally used and pharmaceutically acceptable carrier in the art. Non-limiting examples of the carrier include saline, sterile water, Ringer's solution, buffered saline, albumin injection solution, dextrose solution, maltodextrin solution, glycerol, ethanol, etc. These may be used alone or in combination of two or more thereof. The carrier may include a non-naturally occurring carrier.

In addition, if necessary, other conventional additives such as antioxidants, buffers and/or bacteriostatic agents, etc. may be added and used, and diluents, dispersants, surfactants, binders, lubricants, etc. may be additionally added to be used by being formulated into injectable formulations such as aqueous solutions, suspensions, emulsions, etc., and pills, capsules, granules, tablets, etc.

In addition, the pharmaceutical composition of the present invention may include a pharmaceutically effective amount of cardiac stem cell spheroids. As used herein, the term "pharmaceutically effective amount" refers to an amount sufficient to treat a disease at a reasonable benefit/risk ratio applicable to medical treatment, and generally, an amount of 0.001 mg/kg to 1,000 mg/kg, preferably 0.05 mg/kg to 200 mg/kg, and more preferably 0.1 mg/kg to 100 mg/kg may be administered once to several times daily. However, for the purposes of the present invention, it is preferable that a specific therapeutically effective amount for a particular patient is applied differently depending on various factors such as the type and extent of the reaction to be achieved, whether other agents are used in some cases, specific compositions, the age, weight, general health status, gender and diet of the patient, the administration time, administration route and the ratio of the composition, duration of treatment, and drugs used with or concurrent with the specific composition, and similar factors well-known in the medical field.

The pharmaceutical composition of the present invention may be administered as an individual therapeutic agent or in combination with other therapeutic agents, and may be administered sequentially or simultaneously with conventional therapeutic agents. It is important to administer an amount that can achieve the maximum effect in a minimum amount without causing side effects by taking all of these factors into consideration, and it can be easily decided by those skilled in the art.

As used herein, the term "injection" refers to introducing the pharmaceutical composition of the present invention to a patient in any suitable manner, and the injection route of the composition of the present invention may be administered via various routes as long as it can reach the desired tissue.

The method of injecting the pharmaceutical composition according to the present invention is not particularly limited and may be used in accordance with a method commonly used in the art. The pharmaceutical composition according to the present invention may be prepared in various formulations depending on the desired method of injection.

The injection frequency of the composition of the present invention is not particularly limited, but may be injected once a day or several times by dividing the dose.

In another aspect, the present invention provides a method for ameliorating or treating ischemic heart disease, comprising injecting the spheroid obtained through the preparation method into the heart of a subject.

As used herein, the terms "cardiac stem cell", "medium", "inhibition of cell adhesion", "seed", "cardiac stem cell spheroid", and "ischemic heart disease" are as described above.

As used herein, the term "subject" may refer to any animal, including humans that already have or are likely to develop ischemic heart disease. The animal may be a human and also a mammal such as a cow, a horse, a sheep, a pig, a goat, a camel, an antelope, a dog, a cat, etc. that require treatment of similar symptoms, but is not limited thereto.

The prevention or treatment method of the present invention may specifically include injecting the composition in a pharmaceutically effective amount to a subject with or at risk of developing ischemic heart disease.

Figure 10:
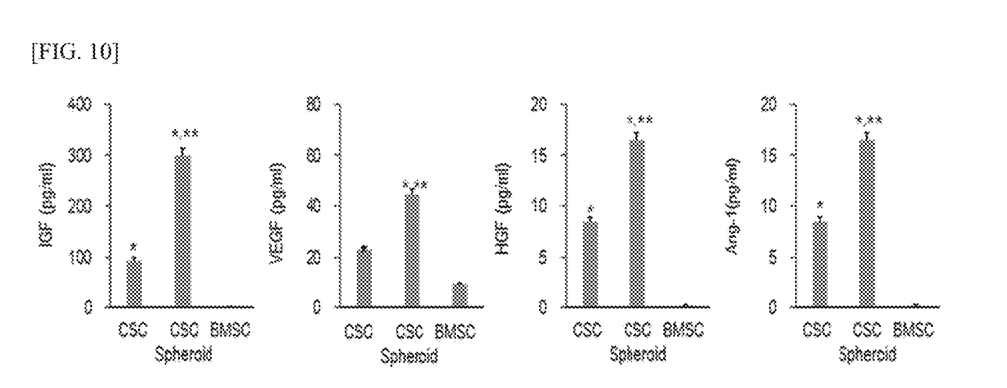
FIG. 10 is a graph showing the results of quantitative analysis of myocardial regeneration factors of cardiac stem cell spheroids and monolayer culture; CSC: cardiac stem cell, CSC Spheroid: cardiac stem cell spheroid, BMSC: bone marrow-derived stem cell.

In one example of the present invention, by injecting the cardiac stem cell spheroid into the heart of a myocardial infarction animal model, it was confirmed that the in vivo myocardial regeneration ability was improved through the increase in the thickness of the left ventricle and the reduction of fibrosis (FIG. 10).

DETAILED DESCRIPTION

Hereinafter, the present invention will be described in detail by the following examples. However, the following examples are only for illustrating the present invention, and the scope of the present invention is not limited by the following examples.

Example 1. Experiment Preparation 1.1 Obtaining Cardiac Stem Cells Derived from Heart Tissue After approval from the ethics committee at Inje University College of Medicine, cardiac stem cells (CSCs) were isolated from adult myocardium. Isolation of CSCs was performed using the method suggested in KR10-1389850. The myocardium, which was donated from a brain-dead patient, was cut into 1 mm$^3$ sections after removing the surrounding epicardium and the endocardium, and washed 5 times with Dulbecco's phosphate-buffered saline (DPBS) solution. Thrombin (Sigma-Aldrich, Seoul, Korea) was dissolved in Dulbecco's Modified Eagles Media (DMEM, Invitrogen, Seoul, Korea) to prepare a 1 unit/mL thrombin solution. Human plasma-derived fibrinogen (Green Cross, Seoul, Korea) was dissolved in DMEM to prepare a 0.25% fibrinogen solution. The cut myocardium was dispersed in 0.25% thrombin solution, mixed with an equal amount of 0.25% fibrinogen solution, and reacted in a 37° C. incubator for 2 hours to form a gel after transferring 10 mL of the mixed solution to a 100-mm culture vessel. After a fibrin hydrogel was formed, 10 mL cell culture solution was added. The cell culture solution was prepared with a composition of 90% DMEM (WELGENE, Gyeongsan, Korea), 10% fetal bovine serum (FBS; Gibco, Seoul. Korea), 10 ng/mL epidermal growth factor (EGF, Peprotech. Seoul, Korea), 2 ng/mL basic fibroblast growth factor (bFGF. Peprotech, Seoul, Korea), 10 ng/mL insulin-like growth factor (IGF, Peprotech, Seoul, Korea), and 10 µg/mL gentamicin (Invitrogen). Afterwards, the culture dish was incubated for 2 weeks while stirring at 30 rpm on an orbital shaker. The fresh cell culture solution was changed every 2 days. CSCs moved and grew from myocardial sections into fibrin hydrogels, and after fibrin hydrogel was digested using 10,000 unit urokinase (Green Cross), cells that released were recovered. Recovered CSCs were amplified and cultured by conventional monolayer culture method. While cells were in a concentrated condition at 80% or more, the cells were removed from the culture vessel and sub-cultured using 0.05% trypsin/EDTA (Sigma-Aldrich, Seoul, Korea).

1.2 Preparation for Cardiac Stem Cell Culture

In order to culture the cardiac stem cells obtained through Example 1, a medium containing Dulbecco's modified Eagle's medium (DMEM), calf serum, DMSO, and L-ascorbic acid was used. Culture vessels in which a cell culture site is coated with a material for lowering cell adhesion were used.

Example 2. Establishment of Optimal Condition for Preparation of Cardiac Stem Cell Spheroid 2-1. Evaluation of Spheroid Formation Ability of Cardiac Stem Cells According to where Heart Tissue is Obtained In order to confirm the spheroid formation ability of cardiac stem cells according to where the heart tissue is obtained, after cardiac stem cells were obtained from a cardiac tissue obtained from auricle, atrium, and apex in the same manner as in Example 1-1, cardiac stem cells of 2×10$^5$ cells/cm$^2$ were suspended in a medium composed of 98.9% DMEM, 1% fetal bovine serum, 0.1% DMSO, and 50 µM ascorbic acid, and then were seeded and cultured in a 24-multiwell tissue culture vessel (Ultra-Low Attachment Surface, Corning, Lowell, Mass.) that inhibits cell adhesion. To compare the shape of cultured spheroids, H&E and DAPI staining was performed and cardiomyocyte differentiation ability was confirmed by immunostaining to compare the regeneration possibility of heart tissue.

Figure 1:
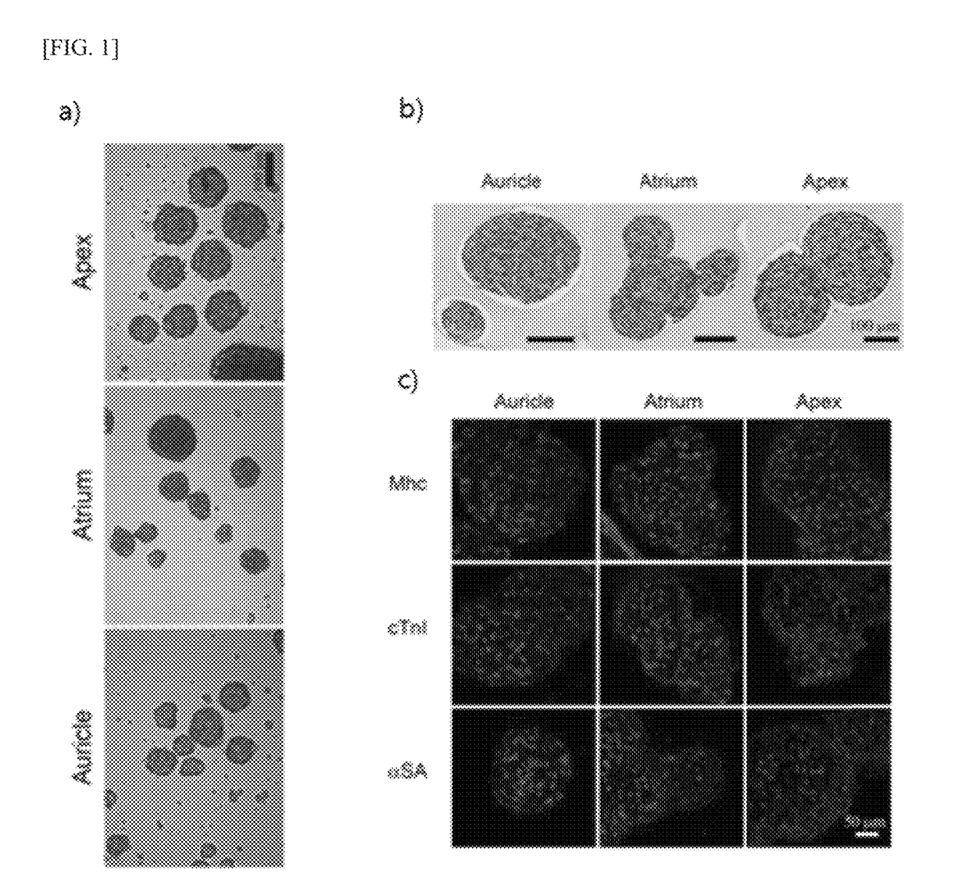
FIG. 1 is a graph showing the formation ability of cardiac stem cell spheroids according to the location in the heart: a) cardiac stem cell spheroids by location in the heart confirmed by DAPI staining, b) cardiac stem cell spheroids by location in the heart confirmed by H&E staining, c) cardiomyocyte-specific protein expression levels of cardiac stem cell spheroids by location in the heart confirmed by immunostaining; Auricle: the auricle of the heart, Atrium: the atrium of the heart, Apex: the apex of the heart, Mhc: myosin heavy chain, cTnI: cardiac troponin I, αSA: alpha sarcomeric actinin.

As a result, as shown in FIG. 1, the difference in the shape of cardiac stem cell spheroids and differentiation capacity to cardiomyocyte according to where the heat tissue was obtained could not be confirmed.

2-2. Evaluation of Spheroid Formation Ability of Cardiac Stem Cells by Serum Concentration To determine the spheroid formation ability of cardiac stem cells according to serum concentrations, cardiac stem cells of 1×10$^5$ cells/cm$^2$ were suspended in a medium composition composed of 98.9% DMEM, 0.1% DMSO, 50 µM ascorbic acid, and fetal bovine serum (0%, 1%, 10%, respectively), and then seeded in a cell adhesion-inhibition container and cultured for 3 days. The shape of cultured spheroids was confirmed through an optical microscope.

As a result, as shown in FIG. 2, spheroids were not formed in the normal condition without serum, and spheroids were not uniformly formed at a 10% serum concentration that is conventionally used in cell culture, and most spheroids were formed at a uniform size at a 1% serum concentration.

Through the above results, it was confirmed that a low concentration of serum conditions of about 1% is necessary to prepare spheroids of uniform size.

2-3. Confirmation of Cell Damage According to Culture Period of Cardiac Stem Cell Spheroids To confirm damage of cardiac stem cells according to the culture period of spheroids, spheroids whose cell number was different were suspended in a medium composed of 98.9% DMEM, 1% fetal bovine serum, 0.1% DMSO, and 50 μM ascorbic acid, and then seeded in a cell adhesion-inhibition container, and the morphological change of cardiac stem cell spheroids according to time was confirmed by culturing for 5 days.

As a result, as shown in FIG. 3, the more the number of cells constituting the spheroids, the darker low-oxygen hypoxiccore was observed, and overall, while it was confirmed that the shape of the spheroids remained stable or structurally stabilized to show a more spherical structure (obvious spherical boundary) for 3 days, it was confirmed that when cultured for 5 days or more, the spherical aggregate structure was lost by viability reduction (cell death and necrosis) of the cells forming the spheroids.

Through the above results, it was confirmed that the spheroid culture in the low serum state is preferably to be performed within 3 days.

2-4. Confirmation of Cell Damage According to Size of Cardiac Stem Cell Spheroids To confirm the damage of cardiac stem cells according to the size of spheroids, cardiac stem cell spheroids having a cell number of 500, 1,000, 2,000, and 5,000, respectively, were cultured for 3 days, and viable cells (green) and dead cells (red) were stained with Live and Dead assay.

As a result, as shown in FIG. 4, while the size of spheroids partially decreased over time, this was judged to be an increase in the density due to structural stabilization, and no significant decrease was confirmed. In addition, when the spheroids were 180 μm to 200 μm or more, the necrosis of cells was confirmed in the center of spheroids, and when the cell number of 1 spheroid was 2.000 or more, the size was confirmed to be 180 μm to 200 μm.

Through the above results, it was confirmed that for the efficient preparation of spheroids, it is preferable to prepare spheroids having a size of less than 200 μm and composed of a cell number of less than 2.000.

2-5. Confirmation of Cell Damage According to Seeding Density of Cardiac Stem Cells To determine the damage of cardiac stem cells according to the seeding density of cardiac stem cells, each of $0.5 \times 10^5$ cells/cm$^2$, $1 \times 10^5$ cells/cm$^2$, $1.5 \times 10^5$ cells/cm$^2$, $2 \times 10^5$ cells/cm$^2$, and $5 \times 10^5$ cells/cm$^2$ were suspended in a medium composed of 98.9% DMEM, 1% fetal bovine serum, 0.1% DMSO, and 50 μM ascorbic acid and cultured for 3 days after seeding in a cell adhesion-inhibition container, and the change was confirmed.

As a result, as shown in FIG. 5, as the number of cardiac stem cells seeded per unit area increased, the size of formed spheroids increased, and the size of spheroids decreased as the density of spheroids themselves increased that were formed over time, but it was confirmed to be not significant. In addition, as a result of evaluating caspase 3/7 activity to quantify apoptotic change according to the seeding density, it was confirmed that the activity of caspase 3/7 significantly increased above a specific seeding density.

Through the above results, in order to efficiently prepare cardiac stem cell spheroids, it was confirmed that it is preferable to use a cell seeding density of $2 \times 10^5$ cells/cm$^2$ or less.

2-6. Spheroid Size Distribution by Seeding Density and Spheroid Size Change by Culture Period To determine the size distribution of spheroids according to seeding density and culture period, each of $0.5 \times 10^5$ cells/cm$^2$, $1 \times 10^5$ cells/cm$^2$, $1.5 \times 10^5$ cells/cm$^2$, $2 \times 10^5$ cells/cm$^2$, and $5 \times 10^5$ cells/cm$^2$ were suspended in a medium composed of 98.9% DMEM, 1% fetal bovine serum, 0.1% DMSO, and 50 μM ascorbic acid and cultured for 3 days after seeding in a cell adhesion-inhibition container. Formed spheroids that were formed by 1 day interval were dropped on a coverglass bottom 6-well plate (SPL, Korea) in a seeding form and observed by a microscope, and the size of the formed spheroids was analyzed by imagej software using images taken at random points, and 100 samples were taken from each group to determine the size distribution.

As a result, as shown in FIG. 6a, the distribution of the increasing size of formed spheroids was confirmed as the cardiac stem cells seeded per unit area increased. For the size change with time, a trend was confirmed in which as time passed, the fraction of large spheroids increased, and it is considered to be due to the low cell adhesion of the culture vessel, the binding and aggregation between the formed spheroids, etc. While the size distribution of the formed spheroids is mainly concentrated in 50 μm to 150 μm to the seeding density of $2 \times 10^5$ cells/cm$^2$, it was confirmed that spheroids with a size of 200 μm or more appeared, in which the central necrosis of spheroids appeared, from the seeding density of $2 \times 10^5$ cells/cm$^2$ or more.

In addition, as shown in FIG. 6B comparing only the spheroid fractions of 200 μm or more, at seeding densities of $2 \times 10^5$ cells/cm$^2$, spheroids of 200 μm or more having a high incidence of cell death were rarely observed or insignificant, but at seeding densities of $5 \times 10^5$ cells/cm$^2$, it was confirmed that the fraction was shown to be markedly high.

To summarize the experimental results obtained in Example 2, the optimal form of preparing cardiac stem cell spheroids is to prepare spheroids by seeding cardiac stem cells in a medium condition composed of 1% fetal bovine serum at a cell seeding density of $2 \times 10^5$ cells/cm$^2$ or less in a cell adhesion-inhibition container and culture within 3 days to be constituted with a spheroid size of less than 200 μm or a cell number of less than 2,000.

Example 3. Confirmation of Pharmacological Activity of Cardiac Stem Cell Spheroids 3-1. Analysis of Pharmacological Activity Factors Related to Myocardial Regeneration of Cardiac Stem Cells and Bone Marrow-Derived Stem Cells To compare the myocardial regeneration efficacy of cardiac stem cells with other stem cells, bone marrow-derived and cardiac stem cells of $1 \times 10^5$ cells/cm$^2$ were suspended in a medium composed of 98.99/c DMEM, 1% fetal bovine serum, 0.1% DMSO, 50 μM ascorbic acid, seeded in a cell adhesion-inhibition container, and cultured for 1 day to confirm the expression levels of the pharmacological activity factors of each cell.

Figure 7:
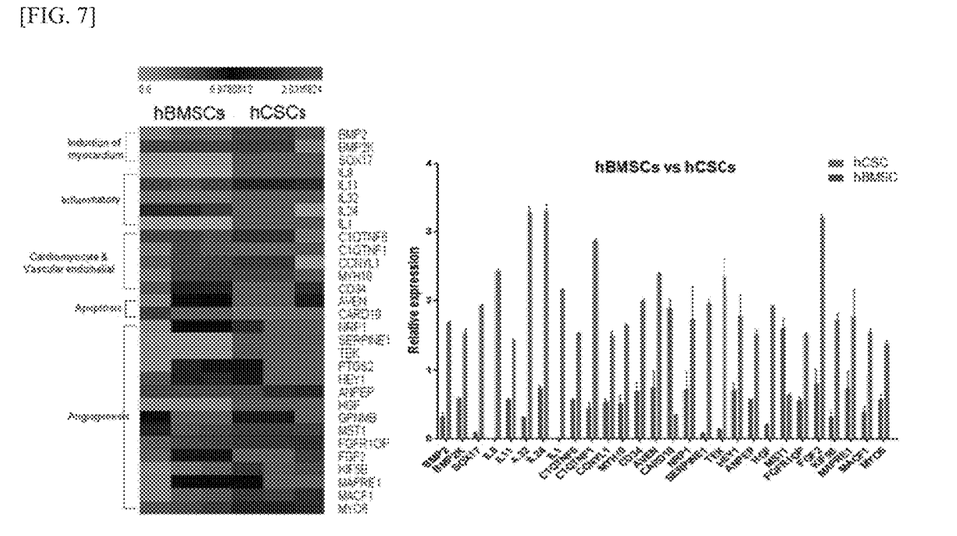
FIG. 7 is a graph comparing the expression levels of pharmacological activation factors of cardiac stem cells and bone marrow-derived stem cells; hBMSC: human-derived bone marrow-derived stem cell, hCSC: human-derived cardiac stem cell.

As a result, as shown in FIG. 7, it was confirmed that the expressions of myocardial differentiation factors (BMP2, SOX17) and angiogenesis factor mRNA (FGF2, HGF, HEY1, PTGS2, NRP1, C1QTNF1,6) were significantly high in cardiac stem cells compared to bone marrow-derived stem cells, and in contrast, the expression of apoptosis-related enzyme (CARD10) was found to be significantly lower. In addition, the expression of anti-inflammatory and immunosuppressive mRNAs (IL-1, 8, 11, 24, 32) was higher in cardiac stem cells than in bone marrow-derived stem cells.

Based on the above results, it was confirmed that cardiac stem cells showered superior cellular characteristics as a therapeutic agent for myocardial regeneration than bone marrow-derived stem cells.

3-2. Analysis of Pharmacological Factors Related to Myocardial Regeneration According to Formulation of Cardiac Stem Cell Spheroids To confirm the pharmacological activity of cardiac stem cells formulated as spheroids, the expression levels of pharmacological activity factors of spheroids and monolayer cultured cardiac stem cells.

As a result, as shown in FIG. 8, it was confirmed that the expressions of myocardial differentiation factors (BMP2,6 and SOX4,9) and angiogenesis factor mRNA (GPNMB, ESM1, FMNL3, HEY1, PTGS2, MGP) increased in spheroids compared to monolayer culture, the mRNA expression of apoptosis-related enzyme (CASP1) decreased, and the expression of anti-inflammatory and immunosuppressive cytokines (IL-24) increased.

Through the above results, it was confirmed that the cellular characteristics changed in the direction of improving the regenerative therapeutic ability and cardiac stem cells and promoting the myocardial differentiation ability when preparing spheroids.

3-3. Analysis of Angiogenesis Factors According to Formulation of Cardiac Stem Cell Spheroids To confirm the angiogenesis inducing ability according to the formulation of cardiac stem cell spheroids, cardiac stem cells of $1 \times 10^5$ cells/cm$^2$ were suspended in a medium composed of 98.9% DMEM, 1% fetal bovine serum, 0.1% DMSO, and 50 µM ascorbic acid, seeded in a cell adhesion-inhibition container, and cultured for 1 day by a spheroid culture method. Cultured monolayer cells and the expression levels of angiogenesis factors of spheroids were compared using Proteome Profiler Angiogenesis kit (R&D systems).

Figure 9:
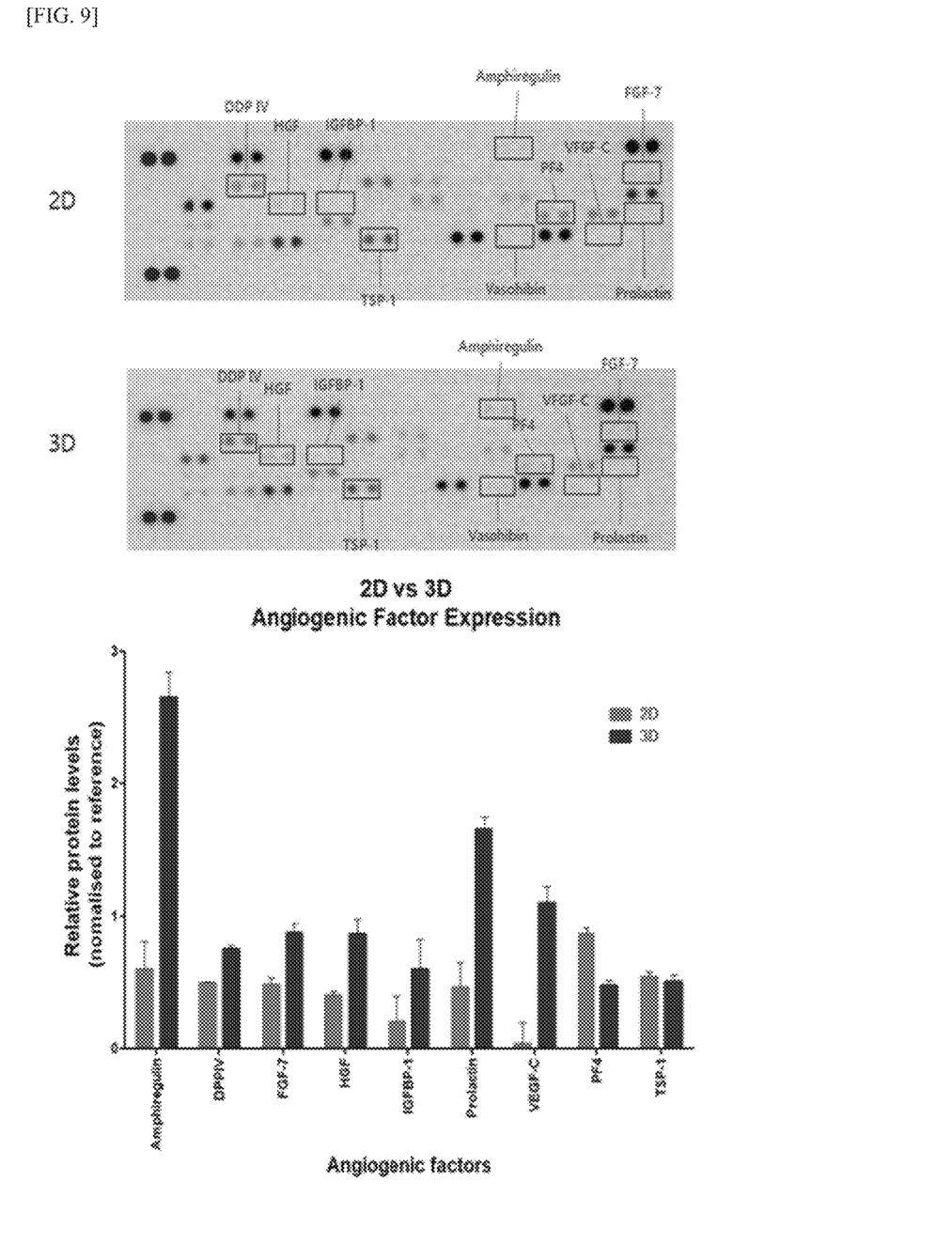
FIG. 9 is a graph comparing the expression levels of angiogenesis factors of cardiac stem cell spheroids and monolayer culture; 2D: cardiac stem cell monolayer culture, 3D: cardiac stem cell spheroid.

As a result, as shown in FIG. 9, whereas it was confirmed that the expression of Amphiregulin, DPPIV, FGF-7, HGF, IGFBP-1, Prolactin, and VEGF-C that are proangiogenic factors increased in spheroids compared to monolayer cultured cells, the expressions of Platelet Factor-4 (PF4) and Thrombospondin-1 (TSP-1) which are anti-angiogenic factors decreased in spheroids, and it was confirmed that cardiac stem cells in the form of spheroids has much stronger angiogenesis inducing ability.

3-4. Quantitative Analysis of Myocardial Regeneration Factors According to Formulation of Cardiac Stem Cell Formulation To quantitatively confirm the myocardial regeneration factors of cardiac stem cells that were formulated as spheroids, the expression levels of myocardial regeneration factors of cardiac stem cell spheroids and mono-cultured cardiac stem cells were determined using bone marrow-derived mesenchymal stem cells (BMSC) as a control group. The key factors related to myocardial regeneration among the bioactive factors secreted from spheroids were quantitatively analyzed using ELISA method.

As a result, as shown in FIG. 10, all of IGF, VEGF, HGF, and Ang-1 from spheroids significantly increased in hCSC comparatively, and it was confirmed that hCSC myocardial regeneration function could be strengthened via spheroid formation, and it was confirmed to have the myocardial regeneration factor secretion ability of 300 times to several tens compared to BMSC.

3-5. Evaluation of Anti-Inflammatory Activity According to Formulation of Cardiac Stem Cell Spheroids To confirm the anti-inflammatory activity of cardiac stem cells formulated as spheroids, the anti-inflammatory activities of cardiac stem cell spheroids and monolayer cultured cardiac stem cells were determined using bone marrow-derived mesenchymal stem cells (BMSC) as a control group. After concentrating the culture solution secreted from each stem cell, the isolation amount of TNFa and IL1b released from THP-1 cells reduced by LPS was evaluated by ELISA.

Figure 11:
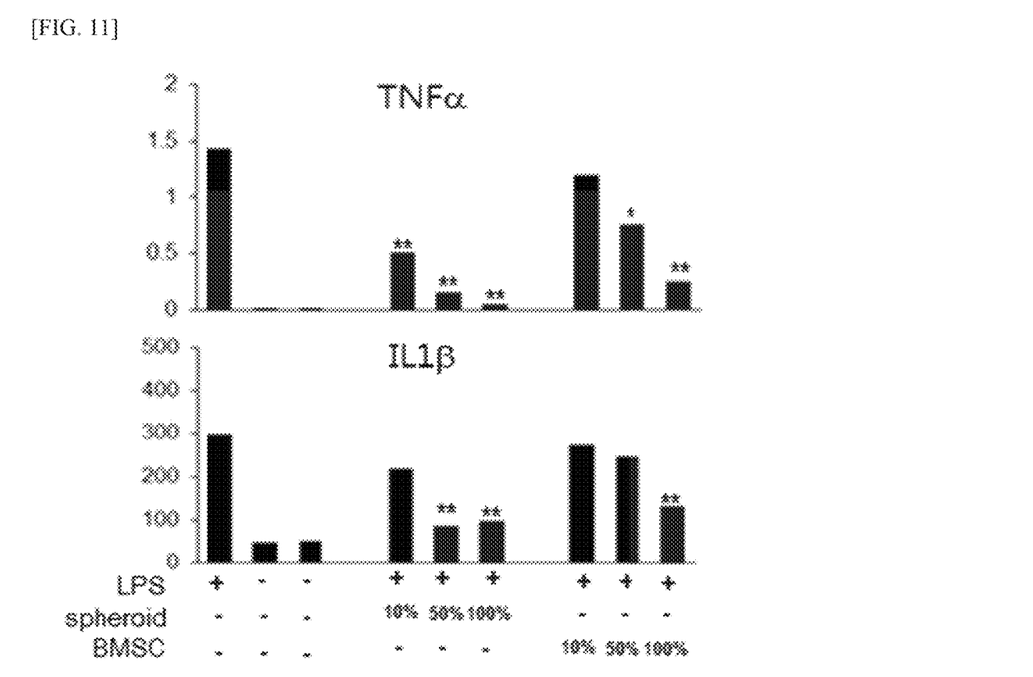
FIG. 11 is a graph showing the results of analysis of anti-inflammatory activity of cardiac stem cell spheroids and monolayer culture; spheroid: cardiac stem cell spheroid, BMSC: bone marrow-derived stem cell.

As a result, as shown in FIG. 11, in case of cardiac stem cell spheroids, it was confirmed that the TNFa and IL1b content was dose-dependently reduced, and the anti-inflammatory activity was shown to be higher than bone marrow-derived mesenchymal stem cells, and it was confirmed that hCSC spheroids have a significant anti-inflammatory mechanism.

3-6. Evaluation of Immunogenicity of Formulation of Cardiac Stem Cell Spheroids

To evaluate the immunogenicity of cardiac stem cells formulated as spheroids, immunogenicity was determined using spheroids, peripheral blood mononuclear cells (PBMC), and bone marrow-derived mesenchymal stem cells (BMSC) as a control group. To evaluate the immunogenicity of each cell, CD4+ TEM and TCM cells that increased by being reduced through co-culturing with T cells were analyzed by a flow cytometer.

Figure 12:
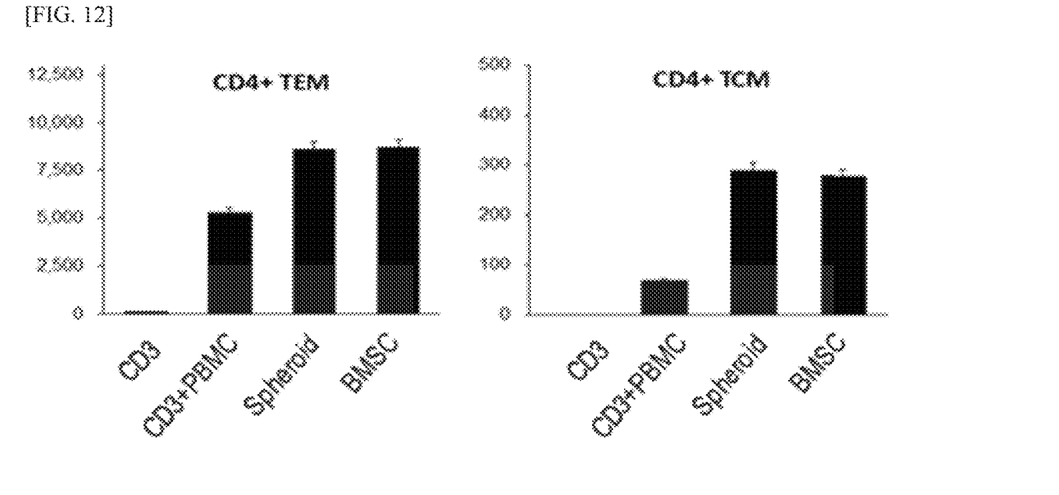
FIG. 12 is a graph showing the results of immunogenicity analysis of cardiac stem cell spheroids and monolayer culture: spheroid: cardiac stem cell spheroid, BMSC: bone marrow-derived stem cell.

As a result, as shown in FIG. 12, even though TEM and TCM proliferation were induced at the same level as allogeneic BMSCs, it did not induce significant proliferation of CD4 T cells, indicating no risk of immunogenicity.

3-7. Evaluation of Myocardial Regeneration Ability of Cardiac Stem Cell Spheroids To confirm the myocardial regeneration ability of cardiac stem cell spheroids in vivo, cardiac stem cells of $1 \times 10^6$ cells/cm$^2$ were suspended in a medium composed of 98.9% DMEM, 1% fetal bovine serum, 0.1% DMSO, and 50 µM ascorbic acid, seeded in a cell adhesion-inhibition container, and cultured for 1 day. After the cultured cardiac stem cell spheroids and cardiac stem cell suspension solution were injected into a myocardial infarction animal model (rat myocardial infarction model), cell engraftment rate and myocardial regeneration ability were evaluated.

Figure 13:
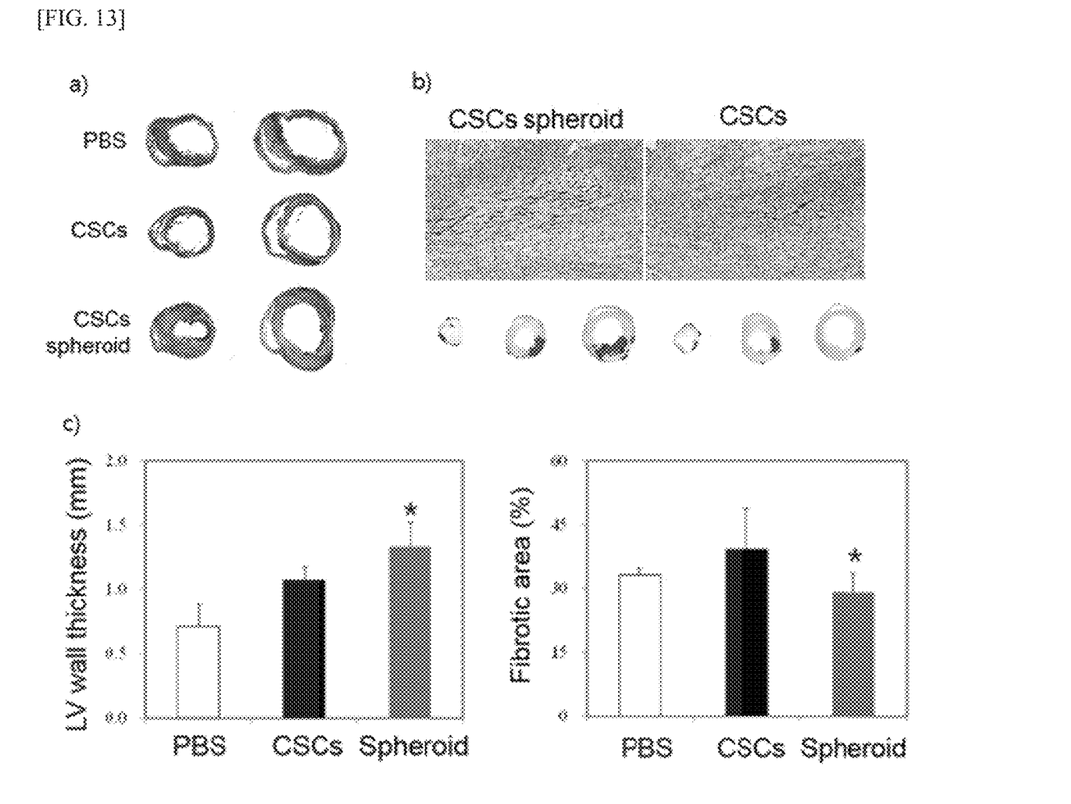
FIG. 13 is a graph confirming the in vivo myocardial regeneration ability of cardiac stem cell spheroids; a) cardiac cross-section after each stem cell injection, b) confirmation of engraftment ratio at the heart after stem cell injection, c) changes in the thickness of the left ventricle and fibrosis site after stem cell injection; PBS: phosphate buffer saline, CSCs: cardiac stem cells, CSCs spheroids: cardiac stem cell spheroids.

As a result, as shown in FIG. 13, the cell engraftment rate increased upon injection of cardiac stem cell spheroids compared to the monolayer cultured cardiac stem cells, and an increase in the thickness of the left ventricle and a decrease in the fibrosis site were confirmed, and thus the improvement of the in vivo myocardial regeneration ability of cardiac stem cell spheroids was confirmed.

3-8. Possibility of Cardiomyocyte-Specific Protein Expression and Functional Enhancement of Cardiac Stem Cell Spheroids To confirm the expression of cardiomyocyte-related proteins of myocardial stem cell spheroids and the effect of wnt3a, which is a myocardial cell differentiation factor, and Dkk-1, which is an inhibition factor, cardiac stem cells of 2 y 10$^5$ cells/cm$^2$ were suspended in a medium composed of 98.9% DMEM, 1% fetal bovine serum, 0.1% DMSO, and 50 µM ascorbic acid, seeded in a cell adhesion-inhibition container, and cultured for 3 days. The expressions of cardiomyocyte-specific proteins and mRNA were confirmed through qRT-PCR and immunofluorescence staining, and each of Wnt3a and Dkk-1 was added to the cultured spheroids to determine the effect on cardiomyocyte differentiation.

Figure 14:
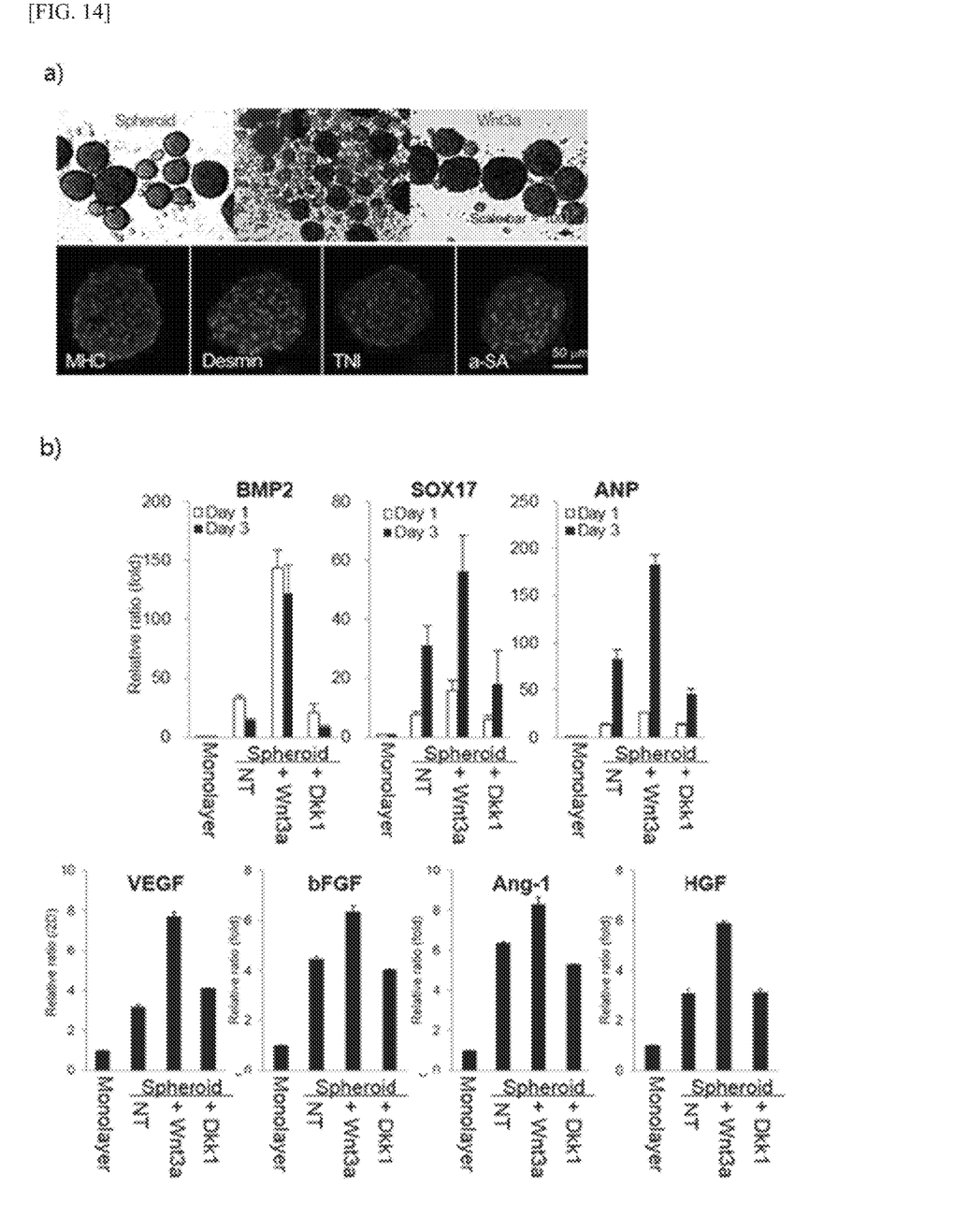
FIG. 14 is a graph confirming cardiomyocyte-specific protein expressions in cardiac stem cell spheroids and functional strengthening by cardiomyocyte differentiation factors; Monolayer: cardiac stem cell monolayer, Spheroid NT: cardiac stem cell spheroid, Spheroid+Wnt3a: cardiac stem cell spheroid+myocardial differentiation factor Wnt3A treatment, Spheroid+Dkk1: cardiac stem cell spheroid+myocardial differentiation inhibitor Dkk1 treatment.

As a result, as shown in FIG. 14, in case of adding wnt3a, which is a cardiomyocyte differentiation factor, the spheroids showing excellent cardiomyocyte-specific mRNA expression levels were found to have the increased expression levels compared with the conventional monolayer culture. On the other hand, in case of adding Dkk-1, the expression level was confirmed to decrease, and the increasing and decreasing effects of the expression were confirmed to be due to Wnt route. Likewise, vascular endothelial cell growth factor (VEGF), basic fibroblast growth factor (bFGF), angiogenin-1 (Ang-1), and hepatocyte growth factor (HGF) also showed similar increasing/decreasing effects, and the corresponding effects were confirmed to be due to Wnt route.

From the above description, those skilled in the art will appreciate that the present invention can be implemented in other specific forms without changing the technical spirit or essential features. In this regard, the embodiments described above are to be understood in all respects as illustrative and not restrictive. The scope of the present invention should be construed that all changes or modifications derived from the meaning and scope of the following claims and equivalent concepts rather than the detailed description are included in the scope of the present invention.

The invention claimed is:

1. A method for preparing a cardiac stem cell spheroid, comprising,
    culturing the cardiac stem cells (CSCs) within 3 days in a culture vessel that inhibits cell adhesion,
    wherein the culture vessel comprises a medium comprising serum at a concentration of 0.1% to 1%, and
    wherein the CSCs are seeded at a density of between $1\times10^2$ cells/cm$^2$ to $2\times10^5$ cells/cm$^2$ in the medium.

2. The method of claim 1, wherein the spheroid prepared above has a size of 50 μm to 200 μm.

3. The method of claim 1, wherein the spheroid prepared above has a cell number of 100 to 2,000.

4. The method of claim 1, wherein the prepared cardiac stem cell spheroid has a low level of caspase 3/7 activity compared to a cardiac stem cell spheroid prepared by seeding at a seeding density of $2.5\times10^5$ cells/cm$^2$ or higher.

5. The method of claim 1, wherein the prepared cardiac stem cell spheroid has less than ½ folds of caspase 3/7 activity compared to a cardiac stem cell spheroid prepared by seeding at a seeding density of $5\times10^5$ cells/cm$^2$ or higher.

6. The method of claim 1, wherein the prepared cardiac stem cell spheroid is characterized in that the expression of cardiac muscle differentiation factors BMP2, BMP6, SOX4 and SOX9 and angiogenesis factors GPNMB, ESM1, FMNL3, HEY1, PTGS2 and MGP is increased; the expression of an apoptotic enzyme CASP1 mRNA is decreased; and the expression of anti-inflammatory and immuno-suppressive cytokine IL-24 is increased, compared to cardiac stem cells cultured by monolayer culture.

7. The method of claim 1, wherein the prepared cardiac stem cell spheroid is characterized in that the expression of proangiogenic factors amphiregulin, DPPIV, FGF-7, HGF, IGFBP-1, prolactin and VEGF-C is increased; and the expression of anti-angiogenic factors platelet factors 4(PF4) and thrombospondin-1 (TSP-1) is decreased, compared to cardiac stem cells cultured by monolayer culture.

8. The method of claim 1, wherein the prepared cardiac stem cell spheroid is characterized in that the expression levels of IGF, VEGF, HGF, and Ang-1 are increased compared to human cardiac stem cells cultured by monolayer culture.

9. The method of claim 1, wherein the prepared cardiac stem cell spheroid is characterized in that the expression of myosin heavy chain (MHC), desmin, troponin (TNI) and alpha-sarcomeric actinin (α-SA) is increased by Wnt signaling compared to cardiac stem cells cultured by monolayer culture.

* * * * *